United States Patent [19]

Westwood

[11] Plant 4,591

[45] Sep. 9, 1980

[54] PEAR TREE

[76] Inventor: Melvin N. Westwood, 2130 NW. Elmwood Pl., Corvallis, Oreg. 97330

[21] Appl. No.: 931,127

[22] Filed: Aug. 4, 1978

[51] Int. Cl.[3] ..... A01H 5/03

[52] U.S. Cl. ..... Plt./36

[58] Field of Search ..... Plt./36

[56] References Cited

U.S. PATENT DOCUMENTS

P.P. 2,489 3/1965 Scanlon ..... Plt./36

*Primary Examiner*—Robert E. Bagwill

*Attorney, Agent, or Firm*—Clarence A. O'Brien; Harvey B. Jacobson

[57] ABSTRACT

A pear tree characterized by its bright red leaves in autumn and its winter hardiness.

3 Drawing Figures

The present discovery relates to a new and distinct clone of pear tree. This invention is a new and distinct clone of pear tree (*Pyrus calleryana* Decn.), with characteristics of value for ornamental uses. It was discovered by the applicant in October 1969 in the course of studies to find disease-resistant rootstocks for domestic pear cultivars. The tree is a chance seedling of unnamed *P. calleryana* parents. It was planted in 1968, in a nursery at the Lewis-Brown Horticultural Research Farm of the Department of Horticulture, at Corvallis, Oreg. It was designated by the code number OPR-250 at the Oregon Experiment Station.

The new clone, which is named Autumn Blaze, produces an upright pyramidal tree of medium size. The tree produces moderate to heavy bloom every year. Fruiting is sparse, and the small mature fruit do not abscise and fall to the ground. The new variety is characterized by its bright red leaves in autumn which differ in color from other *Pyrus calleryana* clones. A color comparison with the Bradford *P. calleryana,* for example, shows the following:

Leaf color on Nov. 8, 1979 at Dayton, Oreg. Autumn Blaze — Cardinal Red 822/1 to Oxblood Red 00823.

Bradford Pear — Fern Green 0862/2 to Spinach Green 0960/2. This new clone has the characteristic disease and pest resistance of other *P. calleryana* trees, but is somewhat more winter hardy than other individuals (including Bradford) of the species. Tests indicate that the xylem parenchyma cells of this new clone are hardy to −27° C., while other *P. calleryana* trees are hardy to about −25° C. In addition, these tests indicate that Autumn Blaze buds were hardy to −34° C., while others of this species were hardy to −28° C.

The general description for all *Pyrus calleryana* trees is the same as that given for Chanticleer. But any two clones derived from different seedlings, as were Chanticleer and Autumn Blaze, have several distinct and measureable differences in the detail of their leaves, growth habit, buds, flowers, and fruit. Autumn Blaze has quite a different growth habit and tree form than Chanticleer. The initial branch angles of Autumn Blaze are nearly 90° with the central leader rather than at 40° as reported for Chanticleer. This difference results in Autumn Blaze being a more spreading tree and somewhat broader at the top than is Chanticleer.

Comparison of Autumn Blaze with the Chanticleer pear reveals several differences. The following measurements of leaves show distinct differences in shape and size:

| | mm Blade length (L) | mm width (W) | L/W ratio | mm Petiole length (P) | blade/petiole (L/P) ratio |
|---|---|---|---|---|---|
| Spur leaves: | | | | | |
| Chanticleer | 52.6 | 51.0 | 1.03 | 45.3 | 1.16 |
| Autumn Blaze | 59.0 | 35.0 | 1.67 | 34.0 | 1.73 |
| Shoot leaves: | | | | | |
| Chanticleer | 71.5 | 63.3 | 1.13 | 37.1 | 1.93 |
| Autumn Blaze | 81.0 | 52.0 | 1.56 | 28.0 | 2.91 |

After selection was made, this clone was propagated asexually by budding and grafting to seedling *P. calleryana* rootstocks. Grafted trees maintained the same characteristics as the original tree.

The accompanying color photograph (FIG. 1) is typical of the young tree in autumn.

Figure 1:
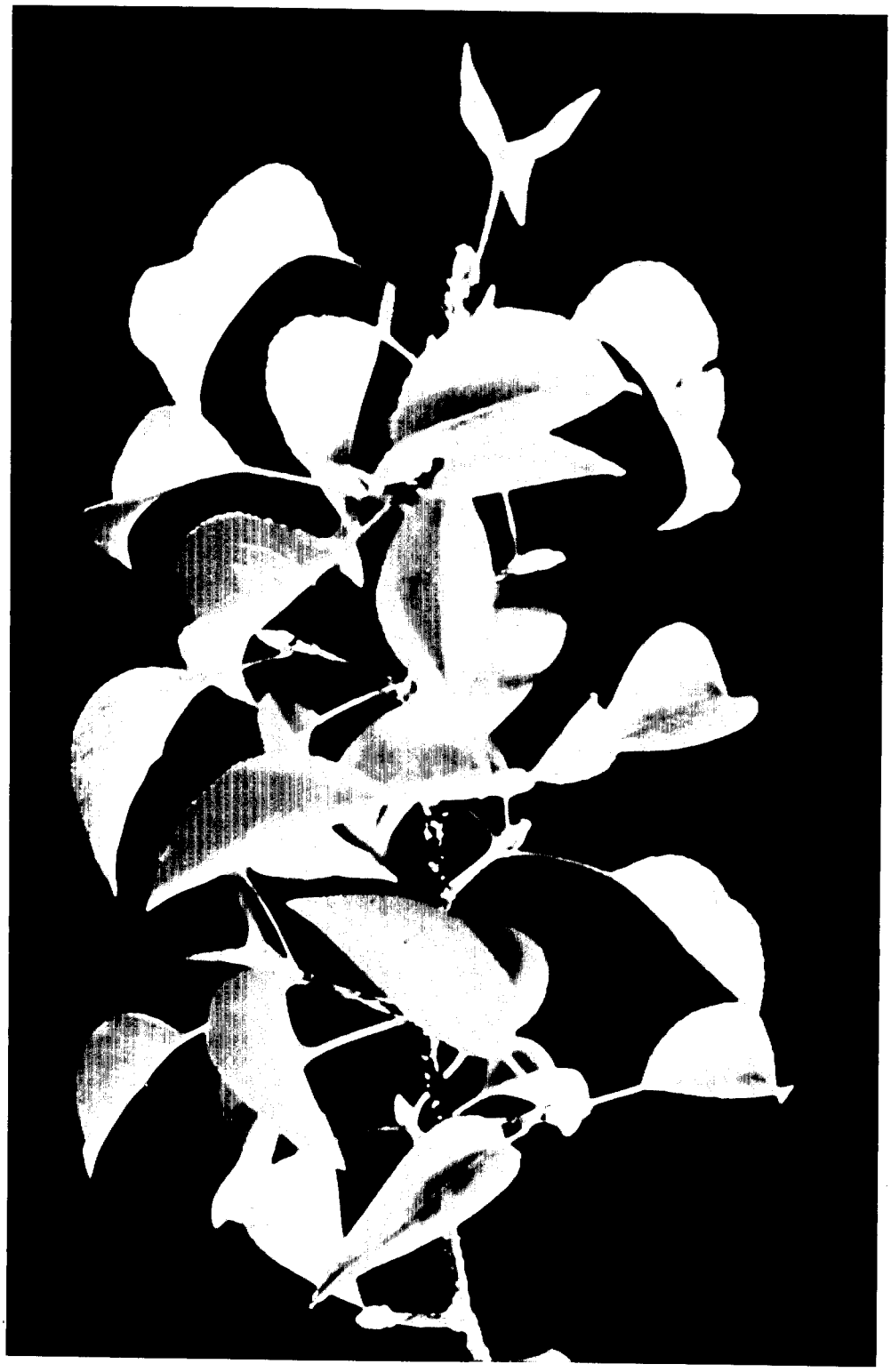
Figure 2:
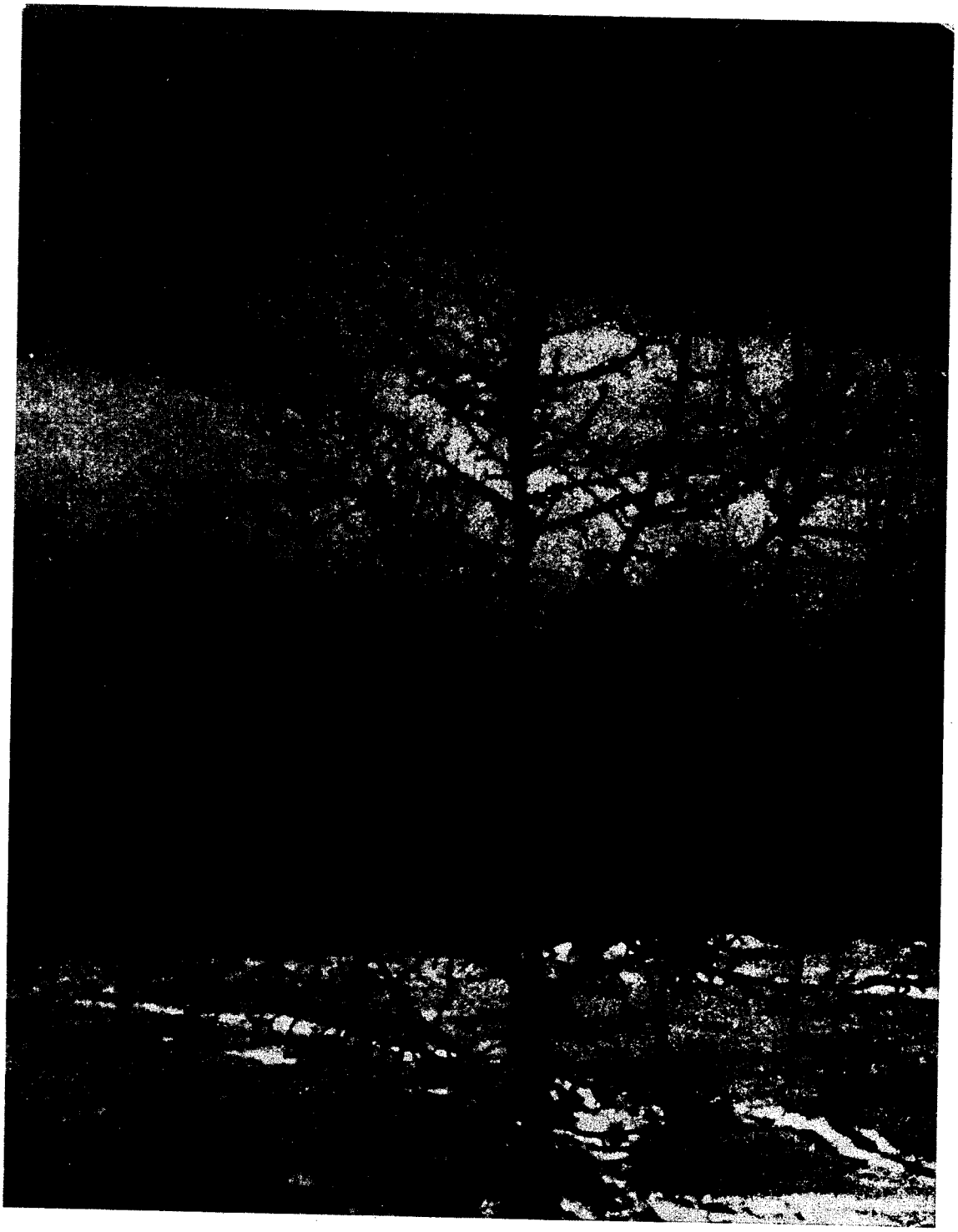
FIG. 2 is an illustration of the tree habit in a dormant state.
Figure 3:
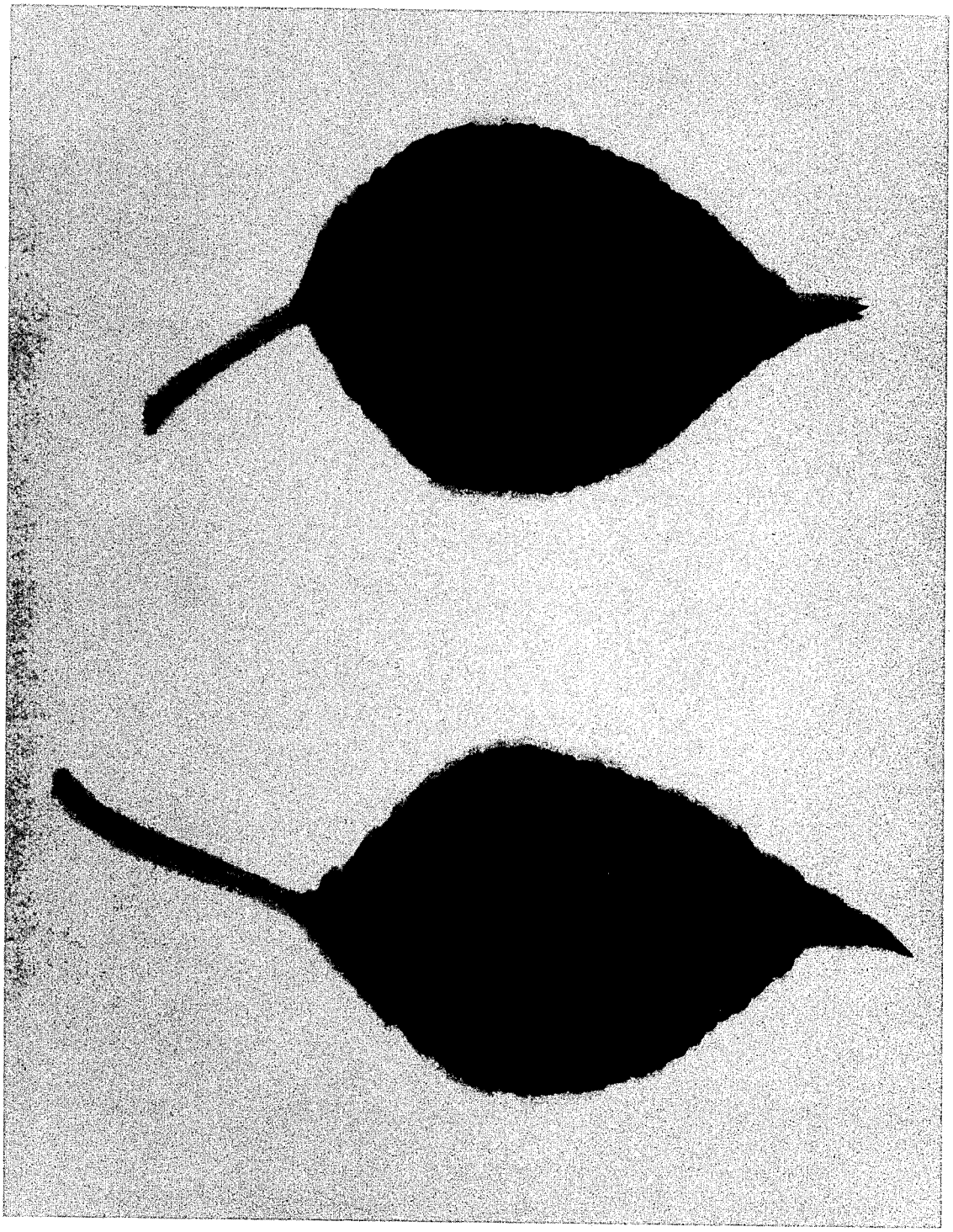
FIG. 3 is an illustration of the leaves in flattened condition.

The following is a detailed description of the new cultivar with the color designation according to the Horticultural Chart issued by the British Colour Council in collaboration with the Royal Horticultural Society.

INFLORESCENCE

Flower buds (dormant): Egyptian Buff (407/2) pubescent, 11.6 mm long, 4.8 mm wide, length/width ratio 2.4 (see photo).

Flower cluster: An indeterminate corymb arising from a mixed bud in which the basal leaves open at the time of anthesis; about 13 flowers per cluster (see photo).

FLOWER

Corolla: 18.5 mm diam. at anthesis; color slight pink (prebloom) to white at anthesis (see photo).

Stamens: Numerous, anthers Rose Red (724/3) before dehiscence (see photo).

FRUIT

Shape: Nearly round, but slightly oblate, length/diam. ratio 0.97.

Size: Longitudinal length 10.1 mm, transverse diam. 10.4 mm.

Color: Russet-Green to Maize Yellow (607/1) when ripe.

Skin: Russeted, with many small white dots (lenticels).

Stem: 11.4 mm long, thin, (0.8 mm diam.), fruit length/-stem length ratio 0.89, no stem basin (attached flush).

Calyx: Deciduous, calyx tube closed.

Flesh: Cream colored, very acid, with a heavy layer of stone cells exterior to the core area.

Carpels: 2, bearing a maximum of 2 seeds per carpel.

Fruit set: Very low (about 5 to 10%), usually only one fruit per cluster.

Maturity season: Fruit ripens about 3 weeks after Delicious apple.

TREE

Tree: Medium sized, upright pyramid in shape.

Leaves: Oval base, with acuminate apex, margin crenate; young leaves reddish tinged, mature ones medium to dark green in summer, turning Cardinal Red 822/1 to Oxblood Red 00823 in autumn; spur leaves about 59 mm long, 35 mm wide, length/width ratio 1.67, petiole about 34 mm long, blade length/petiole length ratio 1.73; shoot leaves about 81 mm long, 52 mm wide, length/width ratio 1.56, petiole about 28 mm long, blade length/petiole length 2.91.

Having thus disclosed my invention, I claim:

1. A new and distinct variety of pear tree characterized by its bright red leaves in autumn and its resistance to most pear pests and diseases.

* * * * *